United States Patent
Kaiser et al.

(10) Patent No.: US 7,741,512 B2
(45) Date of Patent: Jun. 22, 2010

(54) PROCESS FOR THE PREPARATION OF CARBONYLATION PRODUCTS

(75) Inventors: Harry Kaiser, Leimen (DE); David John Law, Beverley (GB); Stephan Andreas Schunk, Heidelberg (DE); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 12/226,150

(22) PCT Filed: Mar. 27, 2007

(86) PCT No.: PCT/GB2007/001113
§ 371 (c)(1),
(2), (4) Date: Oct. 9, 2008

(87) PCT Pub. No.: WO2007/128955
PCT Pub. Date: Nov. 15, 2007

(65) Prior Publication Data
US 2009/0182165 A1    Jul. 16, 2009

(30) Foreign Application Priority Data
Apr. 12, 2006  (GB) ................. 0607394.4

(51) Int. Cl.
*C07C 51/12* (2006.01)
*C07C 51/14* (2006.01)
*C07C 67/36* (2006.01)

(52) U.S. Cl. .............. 560/232; 562/520; 562/519

(58) Field of Classification Search ............ None
See application file for complete search history.

(56) References Cited

U.S. PATENT DOCUMENTS

| 3,780,121 | A |   | 12/1973 | Crone et al. |         |
|-----------|---|---|---------|--------------|---------|
| 4,112,008 | A | * | 9/1978  | Marcilly     | 585/458 |
| 4,151,120 | A |   | 4/1979  | Marcilly     |         |
| 4,612,387 | A | * | 9/1986  | Feitler      | 560/232 |

FOREIGN PATENT DOCUMENTS

| EP | 0 596 632   |   | 5/1994  |
|----|-------------|---|---------|
| FR | 2 41 359    |   | 6/1981  |
| JP | 1-254633    |   | 10/1989 |
| JP | 11-147042   |   | 6/1999  |
| JP | 11-147042 A | * | 6/1999  |
| WO | 2005/105720 |   | 11/2005 |

OTHER PUBLICATIONS

International Search Report for PCT/GB2007/001095, mailed Jun. 25, 2007.
Written Opinion of the International Searching Authority for PCT/GB2007/001095, mailed Jun. 25, 2007.
Shibata, J. et al., "Influence of Zeolite Support on Activity Enhancement by Addition of Hydrogen for SCR of NO by Propane Over Ag-Zeolites" Applied Catalysis B: Environmental, vol. 54, No. 3, (Dec. 20, 2004).

* cited by examiner

*Primary Examiner*—Paul A Zucker
(74) *Attorney, Agent, or Firm*—Nixon & Vanderhye

(57) ABSTRACT

Process for preparing an aliphatic carboxylic acid having (n+1) carbon atoms, where n is an integer up to 6, and/or the ester derivative thereof by contacting an aliphatic alcohol having n carbon atoms and/or a reactive derivative thereof selected from dialkyl ether, ester of the alcohol and an alkyl halide with carbon monoxide in the presence of a catalyst. The catalyst consists of mordenite which has been ion-exchanged or otherwise loaded with silver.

20 Claims, No Drawings

PROCESS FOR THE PREPARATION OF CARBONYLATION PRODUCTS

This application is the U.S. national phase of International Application No. PCT/GB2007/001113, filed 27 Mar. 2007, which designated the U.S. and claims priority to GB Application No. 0607395.1, filed 12 Apr. 2006, the entire contents of each of which are hereby incorporated by reference.

This invention relates to a process for preparing carbonylation products such as aliphatic carboxylic acids and/or derivatives thereof by reacting the corresponding alcohol and/or a reactive derivative thereof with carbon monoxide in the presence of a metal loaded mordenite catalyst.

The preparation of acetic acid from methanol and carbon monoxide is a well known carbonylation process and is carried out commercially. On a commercial scale the manufacture of acetic acid may be operated as a homogeneous liquid-phase process in which the carbonylation reaction is catalysed by a soluble rhodium/iodide complex and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

GB 1185453 discloses certain multiphase catalysts comprising a catalytically active metal including inter alia copper, rhodium and iridium supported on a wide range of carrier materials including silicas, aluminas, carbons, zeolites, clays and polymers. These multiphase catalysts are taught as being useful in the heterogeneous gas phase carbonylation of methanol to acetic acid in the presence of a halide promoter. A similar process is disclosed GB 1277242, although neither patent exemplifies the use of zeolites in such a process.

U.S. Pat. No. 4,612,387 discloses a process for making monocarboxylic acids and esters comprising contacting carbon monoxide with a monohydric alcohol having from 1 to 4 carbon atoms in the presence of a crystalline aluminosilicate zeolite having a silica to alumina ratio of at least about 6 and a constraint index within the range of 1 to 12 under a pressure of at least 1 atmosphere. The most preferred zeolites according to this definition are ZSM-5, ZSM-11, ZSM-12, ZSM-38 and ZSM-35 with ZSM-5 being particularly preferred.

J Catalysis, 71, 233-43 (1981) discloses the use of photoelectron spectroscopy (ESCA) to determine the activity of a rhodium mordenite catalyst and other supported rhodium catalysts towards carbonylation of methanol to acetic acid.

DE 3606169 discloses a process for the preparation of acetic acid, methyl acetate and/or dimethyl ether by carbonylation of anhydrous methanol, methyl acetate and/or dimethyl ether in the presence of cobalt containing zeolites or zeolites mixed with cobalt salts. The carbonylation is optionally carried out in the presence of a halide. The preferred zeolites are disclosed as being of the pentasil type whose pore sizes are intermediate between that of zeolite A on the one hand and zeolites X and Y on the other.

EP-A-0 596 632 discloses a process for the preparation of an aliphatic carboxylic acid by contacting an alcohol or a reactive derivative thereof with carbon monoxide, substantially in the absence of halogens or derivative thereof, in the presence of a catalyst consisting essentially of a mordenite zeolite which has been ion-exchanged or loaded with copper, nickel, iridium, rhodium or cobalt, characterised in that the process is carried out at a temperature in the range 300° to 600° C. and at a pressure in the range 15 to 200 bars. From the work carried out in EP-A-0 596 632 it was found that copper loaded mordenite provided the best selectivity results.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof. However, the use of zeolites to catalyse the carbonylation reaction is not exemplified.

WO 2005/105720 describes a process for preparing carboxylic acids and derivatives thereof by carbonylating an alcohol or derivative thereof with a mordenite catalyst which has been ion-exchanged or otherwise loaded with copper, nickel, iridium, rhodium or cobalt and which has one or more of gallium, boron and iron as framework modifier elements.

In view of the above-mentioned prior art, the problem to be solved is to develop a heterogeneous gas phase process for preparing carboxylic acids and/or derivatives thereof from alcohols/derivatives thereof and carbon monoxide using a metal loaded zeolite catalyst, which is superior to the best processes using mordenite zeolites previously described.

It has now been found that a mordenite zeolite (hereinafter referred to as mordenite) which has been loaded with silver provides enhanced carbonylation product selectivity (to the carboxylic acid and/or derivatives thereof).

Accordingly, the present invention provides a process for preparing an aliphatic carboxylic acid having (n+1) carbon atoms, where n is an integer up to 6, and/or the ester derivative thereof which comprises contacting an aliphatic alcohol having n carbon atoms and/or a reactive derivative thereof with carbon monoxide in the presence of a catalyst, wherein said catalyst consists of mordenite which has been ion-exchanged or otherwise loaded with silver.

The process of the present invention utilises a silver-modified mordenite catalyst to produce good yields of carboxylic acids and derivatives thereof. It has been surprisingly found that improved activity and/or product selectivity can be achieved by utilising a mordenite which has been modified with silver.

In the process of the present invention an aliphatic alcohol or a reactive derivative thereof is carbonylated with carbon monoxide. The process is particularly applicable to aliphatic alcohols having up to 6, such as up to 3, carbon atoms. A preferred alcohol is methanol.

Reactive derivatives of the alcohol which may be used as an alternative to, or in addition to the alcohol, include dialkyl ethers, esters of the alcohol and alkyl halides. Suitable reactive derivatives of methanol, for example, include methyl acetate, dimethyl ether and methyl iodide. A mixture of an alcohol and the reactive derivative thereof, for example a mixture of methanol and methyl acetate, may also be employed.

The product of the process may be an aliphatic carboxylic acid and/or the ester of the aliphatic carboxylic acid. For example, where the alcohol is methanol, the product predominantly comprises acetic acid but it may also comprise some methyl acetate. Where an ether is used as the reactant, the product will predominantly be an ester. For example, where dimethyl ether is a reactant, the product will predominantly be methyl acetate.

The process is preferably carried out in the presence of water. The feed comprising an alcohol, ester or ether or any combination thereof may also comprise water. Suitably the molar ratio of alcohol:water, such as methanol:water is in the range 50:1 to 2:1, such as 10:1 to 3:1. Where an ester or an ether, such as methyl acetate or dimethyl ether, is used as a feed the molar ratio of water to ester or ether is suitably in the range 1:1 to 1.5:1.

The water may be fed separately to or together with the alcohol and/or reactive derivative. The water may be present in liquid or vapour form.

Depending on the nature of the feed, water may be generated in-situ, for example by the dimerisation of alcohol feed to ethers or via esterification of an alcohol with the carboxylic acid product. Suitably, the amount of generated water may be such that the ratio of alkyl groups derived from the alcohol feed to water is less than or equal to 1.

The purity of the carbon monoxide used is not deemed to be especially critical although it is desirable to use gas mixtures in which carbon monoxide is the main component. The presence of small amounts of impurities such as nitrogen and the noble gases can be tolerated. The carbon monoxide may be used in admixture with hydrogen. Suitably, the ratio of $CO:H_2$ is in the range 1:3 to 15:1 on a molar basis, such as 1:1 to 10:1. For example, mixtures of carbon monoxide and hydrogen as produced by the reforming or partial oxidation of hydrocarbons (synthesis gas) may also be used in the process of the present invention.

The catalyst used in the process of the present invention is a mordenite zeolite which has been ion-exchanged, or otherwise loaded with silver. The structure of mordenite is well known and defined for example in 'Atlas of Zeolite Structure Types' by W M Meier and D H Olson published by the Structure Commission of the International Zeolite Association in 1978. It is further characterised by having a constraint index of 0.4 and a silica to alumina ratio in the range 8:1 to 20:1. It is well known to those skilled in the art that the silica to alumina ratio may be increased by using de-alumination techniques, for example, by hydro-thermal treatment or acid leaching of the mordenite. Mordenite also possesses a characteristic X-ray powder diffraction pattern which will be well known to those skilled in the art.

For the process of the present invention it is preferred that the mordenite has a silica to alumina ratio in the range 10:1 to 30:1, most preferably in the range 15:1 to 25:1 and especially in the range 18:1 to 22:1.

Before use as a catalyst, the mordenite is ion-exchanged or otherwise loaded with silver. The loading of the mordenite by silver may be by any method such as the well-known techniques of ion-exchange, wet impregnation and incipient wetness. If the mordenite is to be ion-exchanged up to 100% of the cation-exchangable sites on the zeolite may be exchanged with Ag+ ions using well known techniques. It is preferred that the remaining cations in the exchanged mordenite are protons hence it is convenient to start the exchange process from the ammonium or hydrogen form.

As an alternative to ion-exchange, the ammonium or hydrogen form of the mordenite can be impregnated with a solution of a silver salt and subsequently dried. Preferably, the mordenite is calcined, for example, in air, at high temperature, for example 500-600° C., after loading or exchange with silver.

The silver loading may be expressed in terms of the degree of substitution in molar terms of the aluminium atoms (the exchange sites) of the mordenite by silver. The amounts used are preferably such as to produce a catalyst having a silver content of 1 to 200 mol % per unit volume of aluminium such as 50 to 150 mol %, such as 50 to 120 mol % and 50 to 80 mol %. A 100 mol % silver equates to a silver loading of 14.18% by weight.

The mordenite may, in addition to silicon and aluminium atoms, contain further elements in the zeolite framework. Such framework modifier elements may be, for example, gallium and/or iron.

The framework modifier elements may be introduced to the framework by any conventional means. For example, the mordenite may be synthesised using suitable precursors for the silicon, aluminium and framework modifier elements. For example, a gallium modified mordenite, may be prepared by reacting together a mixture comprising fumed silica, gallium nitrate and sodium aluminate. Suitable preparation methods are described, for example, in WO 05/105720.

Where a framework modifier element is used, the mordenite may suitably have a ratio of silica to the oxide of the framework modifier element in the range 10:1 to 50:1.

The process of the present invention is preferably carried out by passing methanol vapour and carbon monoxide gas through a fixed or fluidised bed of the catalyst maintained at the desired temperature and pressure.

The process is suitably carried out at a temperature in the range 200 to 600° C., preferably 250 to 400° C.

The process is suitably carried out at a pressure in the range 10 to 200 bar, preferably 10 to 150 bar, such as 25 to 100 bar.

The molar ratio of carbon monoxide to alcohol, such as methanol or reactive derivative is suitably in the range 1:1 to 99:1, such as 1:1 to 30:1.

The Gas Hourly Space Velocity (GHSV) is suitably in the range 500 to 15,000 $h^{-1}$, such as 2000 to 10,000 $h^{-1}$.

The mordenite catalyst is activated prior to use by, for example, subjecting the mordenite catalyst for at least one hour at elevated temperature under flowing nitrogen, carbon monoxide or hydrogen.

If desired, the alcohol and/or reactive derivative feed may be contacted with a bed of alumina or corundum immediately before the bed of mordenite catalyst.

Preferably, the process of the present invention is carried out substantially in the absence of halides, such as iodide. By substantially is meant that the halide content, such as the iodide content of the feed gases and catalyst are less than 500 ppm and preferably less than 100 ppm.

The process may be carried out either as a fixed bed, fluid bed or moving bed process.

The process may be operated as either a continuous or a batch process, preferably as a continuous process.

The carboxylic acid produced by the process of the present invention can be removed in the form of a vapour and thereafter condensed to a liquid. The carboxylic acid can be subsequently purified using conventional techniques, such as distillation.

Where an ester such as methyl acetate is a product of the process, it may be recovered and used as such as a feedstock for other chemical processes, or it may be hydrolysed to the corresponding carboxylic acid using known techniques such as reactive distillation.

The invention will now be illustrated with reference to the following Examples.

EXAMPLES 1 TO 3

Preparation A—Preparation of H-Mordenite

Mordenite with a silica to alumina ratio of 20 (ex Südchemie) was compacted at a pressure of 12 tonnes in a mortar and pestle and then sieved to a particle size fraction of 125 to 160 microns. 2.5 g of the mordenite was then calcined at a temperature of 600° C. under air at a ramp rate of 1° C./min to a temperature of 500° C., held at 500° C. for 30 min, the temperature was increased by 1° C./min to 550° C., held at 550° C. for 30 min, then increased by 1° C./min to 600° C., and held at 600° C. for 180 min.

Preparation B—Preparation of Cu (55) Mordenite

Mordenite with a silica to alumina ratio of 20 (ex Süd-Chemie) was treated with a copper acetate solution, to a molar level corresponding to the substitution of 55% of the protons attached to acid sites by copper, giving a copper loading of 4.88% by weight. 1810 μl of a solution of 1.0 mol/l copper acetate was mixed with 465 μl of water. The LOI (loss on ignition, 600° C.) of the mordenite was measured (typically 10-20%, in this case 13%) to account for the amount of water adsorbed on the mordenite in order to determine the amount of metal solution required to achieve the desired copper loading. The solution was mixed well with the aid of an automatic dispensing system. The mordenite was then impregnated with the copper acetate solution. After the impregnation the mordenite was left at ambient conditions on a shaker for 2 h. After the shaking the copper loaded mordenite was transferred to a forced convection oven (air as atmosphere) at 80° C. for 20 h. After the drying step the copper loaded mordenite was calcined in air and heated at 1° C./min to a temperature of 500° C., held at 500° C. for 30 min, then the temperature was increased by 1° C./min to 550° C., held at 550° C. for 30 min, then increased by 1° C./min to 600° C., held at 600° C. for 180 min followed by cooling to ambient conditions under a stream of air. The copper loaded mordenite was then sieved to obtain particles having a size in the range 125-160 μm Preparation C—Preparation of Ag (55) Mordenite Preparation method B was repeated except that Ag nitrate was used for the impregnation process instead of copper acetate in amounts such that Ag loadings 55 mol % replacement of protons in the mordenite were obtained.

Carbonylation Reactions

Each of the H—, Cu and Ag mordenite catalyst samples prepared as described above was used to prepare carbonylation products by the carbonylation of methanol with carbon monoxide. The experiments were carried out in a pressure flow reactor unit consisting of 16 identical reactors of the type described in for example, WO 2005063372. Prior to the loading of a catalyst sample in the reactor, a bed of corundum of sieve fraction of 125-160 μm was placed in the respective catalyst sample holder. A 1 ml sample of a catalyst was placed on top of the corundum bed. The catalyst sample was covered by a corundum bed of a particle size of 250-500 μm. The catalyst sample was then pressurised to the desired reaction pressure of 30 bar with CO at a flow rate of 66.66 ml/min. The catalyst was then heated at 0.5 deg. C./min to a holding temperature of 220° C., where it was held for a dwell time of 3 hours. Subsequently the temperature was ramped to 300° C. at 0.5 deg. C./min, again followed by a dwell time of 3 hours. At this point catalyst activation is considered complete and the gas feed was switched to a mixture of carbon monoxide and hydrogen with a CO/$H_2$ ratio of 4 at a flow rate of 66.66 ml/min, while methanol was fed at 40 ml/min as a vapour, to obtain a CO:$H_2$:MeOH ratio in the total feed of approximately 80:20:1 on a molar basis. Nitrogen was also introduced at a variable rate of 0-50 ml/min to equalise the pressure swings between the 16 reactor exits. The exit stream from the reactor was passed to a gas chromatograph to determine the concentration of reactants and carbonylation products.

In Example 1 the reaction was allowed to continue for 84.2 hours under conditions of 300° C., 30 bar, a gas hourly space velocity (GHSV) of 4000/h with a feedstock ratio of CO:$H_2$:MeOH of 79.2:19.8:1. At 84.2 hours the MeOH feed was increased from 1 mole % to 2 mole %, giving a feedstock ratio of CO:$H_2$:MeOH of 78.4:19.6:2 and the reaction continued for a total time of 155.2 hours.

In Example 2 the reaction was allowed to continue for 164.4 hours under conditions of 300° C., 30 bar, a gas hourly space velocity (GHSV) of 4000/h with a feedstock ratio of CO:$H_2$:MeOH of 79.2:19.8:1. At 164.4 hours the MeOH feed was increased from 1 mole % to 2 mole %, giving a feedstock ratio of CO:$H_2$:MeOH of 78.4:19.6:2 and the reaction continued for a total time of 233.3 hours.

In Example 3 the reaction was allowed to continue for 168.9 hours under conditions of 300° C., 30 bar, a gas hourly space velocity (GHSV) of 4000/h with a feedstock ratio of CO:$H_2$:MeOH of 79.2:19.8:1. At 168.9 hours the MeOH feed was increased from 1 mole % to 2 mole %, giving a feedstock ratio of CO:$H_2$:MeOH of 78.4:19.6:2 and the reaction continued for a total time of 239.3 hours.

The results for Examples 1 to 3 (H-mordenite, 55 mol % Cu loaded mordenite and 55 mol % Ag loaded mordenite respectively) are given in Table 1 below.

TABLE 1

| Example | Metal promoter | Metal loading (mol %) | Time on Stream (hrs) | STY AcOH (g/kg/h) | STY MeOAc (g/kg/h) |
|---|---|---|---|---|---|
| 1 | None | 0 | 16.8 | 24.8 | 13.8 |
|   |      |   | 155.2 | 3.2 | 32.7 |
| 2 | Cu | 55 | 16.2 | 55.6 | 22.4 |
|   |    |    | 154.4 | 24.4 | 59.4 |
|   |    |    | 233.3 | 12.2 | 83.8 |
| 3 | Ag | 55 | 16.1 | 101.4 | 5.9 |
|   |    |    | 156.3 | 54.6 | 60.8 |
|   |    |    | 239.3 | 22.8 | 129.9 |

EXAMPLES 4 TO 16

Preparation of Cu Mordenite at 5 Mol % and 110 Mol % Loadings

Preparation method B above was repeated except that copper nitrate, Cu($NO_3$)$_2$.3$H_2$O, was used instead of copper acetate in amounts in the impregnation process such that Cu loadings equivalent to 5 mol % and 110 mol % replacement of protons in the mordenite were obtained.

Preparation of Ag Mordenite at 5 Mol % and 110 Mol % Loadings

Preparation method B above was repeated except that silver nitrate was used instead of copper acetate in amounts in the impregnation process such that Ag loadings equivalent to 5 mol % and 110 mol % replacement of protons in the mordenite were obtained Preparation of Ir Mordenite Preparation method B above was repeated except that iridium trichloride hydrate, $IrCl_3$.hydrate, dissolved in water (treated under reflux for ~20 h) was used for the impregnation process instead of copper acetate in amounts such that Ir loadings equivalent to 5 mol %, 55 mol % and 110 mol % replacement of protons in the mordenite were obtained.

Preparation of Ni Mordenite

Preparation method B above was repeated except that nickel nitrate, Ni(NO$_3$)$_2$.6H$_2$O, was used for the impregnation process instead of copper acetate in amounts such that Ni loadings equivalent to 5 mol %, 55 mol % and 110 mol % replacement of protons in the mordenite were obtained.

Preparation of Carbonylation Products

Each of the Cu, Ag, Ni and Ir mordenite catalyst samples prepared as described above and also the H-mordenite, and the Cu (55) and Ag(55) mordenite catalysts as prepared above in Preparations A, B and C respectively was used as the catalyst in the carbonylation of methanol with carbon monoxide. The carbonylation reactions were carried out using the method described above in Examples 1-3 using a feedstock of CO:H$_2$:MeOH in a molar ratio of 79.2:19.8:1. Results for Examples 4 to 16 after approximately 40 hours on stream are given in Table 2 below.

TABLE 2

| Example | Metal promoter | Metal loading (%) | Time on stream (hrs) | STY AcOH (g kg$^{-1}$ h$^{-1}$) | STY MeOAc (g kg$^{-1}$ h$^{-1}$) | STY Acetyls (g kg$^{-1}$ h$^{-1}$) |
|---|---|---|---|---|---|---|
| 4 | none | 0 | 39.2 | 13.0 | 28.0 | 35.7 |
| 5 | Ag | 5 | 41.0 | 43.1 | 31.6 | 68.8 |
| 6 | Cu | 5 | 42.0 | 7.5 | 39.8 | 39.8 |
| 7 | Ir | 5 | 41.8 | 47.2 | 5.4 | 51.6 |
| 8 | Ni | 5 | 40.1 | 12.8 | 31.2 | 38.1 |
| 9 | Ag | 55 | 40.6 | 91.5 | 24.2 | 111.1 |
| 10 | Cu | 55 | 40.9 | 38.1 | 45.5 | 75.0 |
| 11 | Ir | 55 | 40.0 | 23.1 | 4.0 | 26.4 |
| 12 | Ni | 55 | 40.6 | 60.9 | 38.3 | 91.9 |
| 13 | Ag | 110 | 40.7 | 86.1 | 25.0 | 106.4 |
| 14 | Cu | 110 | 41.7 | 75.0 | 16.3 | 88.2 |
| 15 | Ir | 110 | 36.3 | 21.5 | 14.7 | 33.4 |
| 16 | Ni | 110 | 39.8 | 54.6 | 46.4 | 92.2 |

The STY to Acetyls is the sum of the MeOAc and AcOH STY's in AcOH equivalents i.e. STY Acetyls=STY AcOH+{STY MeOAc×(60.05/74.08)}.

As the results of Table 2 show, the use of Ag mordenite provides superior results to those of the Cu, Ir and Ni loaded mordenites and H-mordenite.

The invention claimed is:

1. A process for preparing an aliphatic carboxylic acid having (n+1) carbon atoms, where n is an integer up to 6, and/or the ester derivative thereof which comprises contacting an aliphatic alcohol having n carbon atoms and/or a reactive derivative thereof selected from dialkyl ether, ester of the alcohol and an alkyl halide with carbon monoxide in the presence of a catalyst, wherein said catalyst consists of mordenite which has been ion-exchanged or otherwise loaded with silver.

2. A process according to claim 1 wherein the mordenite has a silver content of 1 to 200 mol % per unit volume of aluminium.

3. A process according to claim 2 wherein the mordenite has a silver content of 50 to 150 mol % per unit volume of aluminium.

4. A process according to claim 1 wherein the mordenite has a silica alumina molar ratio in the range 10:1 to 30:1.

5. A process according to claim 1 wherein the mordenite contains a framework modifier element selected from at least one of gallium and iron.

6. A process according to claim 5 wherein the mordenite has a silica:oxide of the framework modifier element molar ratio in the range 10:1 to 50:1.

7. A process according to claim 1 wherein the alcohol is methanol.

8. A process according to claim 1 wherein the alcohol and/or reactive derivative is contacted with a bed of alumina or corundum immediately before a bed of mordenite catalyst.

9. A process according to claim 1 wherein the carbon monoxide is used as a mixture with hydrogen.

10. A process according to claim 1 wherein water is also fed to the process.

11. A process according to claim 1 wherein the process is carried out substantially in the absence of halides.

12. A process according to claim 1 wherein the process is carried out at a temperature in the range 200 to 600° C.

13. A process according to claim 12 wherein the process is carried out at a temperature in the range 250 to 400° C.

14. A process according to claim 1 wherein the process is carried out at a pressure in the range 10 to 200 bar.

15. A process according to claim 14 wherein the process is carried out at a pressure in the range 25 to 100 bar.

16. A process according to claim 1 wherein the gas hourly space velocity is in the range 2000 to 10,000 h$^{-1}$.

17. A process according to claim 1 wherein the process is operated as a continuous process.

18. A process according to claim 1 wherein the process is carried out as a fixed bed, fluid bed or moving bed process.

19. A process according to claim 1 wherein the carboxylic acid is acetic acid.

20. A process according to claim 1 wherein the process is a process for preparing acetic acid by contacting methanol with carbon monoxide in the presence of hydrogen at a temperature in the range 250 to 400° C. and at a pressure in the range 25 to 100 bar and wherein the mordenite contains 50 to 150 mol % of silver per unit volume of aluminium.

* * * * *